(12) United States Patent
Wharton et al.

(10) Patent No.: US 6,260,426 B1
(45) Date of Patent: Jul. 17, 2001

(54) TEST STAND FOR FUEL COMPONENTS USING LOW VISCOSITY/HIGH FLASHPOINT FUEL LOOK-ALIKE

(75) Inventors: Charles J. Wharton, Darien; Jeffrey E. Hunt, Middlebury, both of CT (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/094,768

(22) Filed: Jun. 15, 1998

(51) Int. Cl.[7] ................................................. G01N 19/00
(52) U.S. Cl. .............................................................. 73/865.9
(58) Field of Search ............................... 73/118.1, 865.9, 73/119 A, 865.6, 117; 252/408.1

(56) References Cited

U.S. PATENT DOCUMENTS

| | | | |
|---|---|---|---|
| 4,122,707 | * 10/1978 | Leunig | 73/118 R |
| 4,387,589 | * 6/1983 | Larson | 73/119 A |
| 4,582,631 | * 4/1986 | Pike | 252/408.1 |
| 4,601,198 | * 7/1986 | Kolitsch | 73/118.1 |
| 5,152,688 | 10/1992 | Cellini . | |
| 6,059,574 | 5/2000 | Wharton et al. . | |

OTHER PUBLICATIONS

McGraw Hill, Encyclopedia of Science & Technology p. 61, Definition of Incompressible.
McGraw–Hill Encyclopedia of Science and Technology p. 367, Fluid–Flow Principles.
Federal–Mogul, National O–Rong Design Guide; chart page, Fluid Compatibility (Hydrocarbon v. Water), where the Nomenclature is Flurocarbon.

* cited by examiner

*Primary Examiner*—Benjamin R. Fuller
*Assistant Examiner*—Octavia Davis
(74) *Attorney, Agent, or Firm*—Mark O. Blut; John D. Lewis

(57) ABSTRACT

A test stand and method for calibrating aircraft fuel components which utilizes a fuel look-alike with a flash point above 180° F. and a viscosity below 2.8. Furthermore, the look-alike has the specific gravity and dielectric constant similar to that of aircraft fuel. An operator sets input parameters and adjusts the components until the desired output parameters are attained.

17 Claims, 3 Drawing Sheets

TEST STAND FOR FUEL COMPONENTS USING LOW VISCOSITY/HIGH FLASHPOINT FUEL LOOK-ALIKE

BACKGROUND OF THE INVENTION

This invention relates generally to a test stand and method for calibrating aircraft fuel components. More specifically, the present invention is directed to a test stand and method which utilizes a fuel look-alike with the properties of aircraft fuel, but without its low flash point.

During development, after initial assembly, and periodically throughout their lives, aircraft fuel components such as fuel pumps and fuel controls need to be evaluated and calibrated to ensure that they are performing within specified parameters of pressure, pressure drop and flow. Aircraft component manufacturers and post-depot overhaul facilities accomplish this calibration with test stands which simulate the operation of aircraft fuel systems. The components on test are mounted on the stand and fuel is passed through them. An operator sets input conditions, and adjusts the components until the desired outputs are reached.

Instead of using actual aircraft fuel, these test stands generally use a fuel "look-alike" which has the properties of aircraft fuel. MIL-F-7024 calibration fluid is normally the fluid of choice. It has a viscosity of 1.9 cs (at 25° C.), a specific gravity of 0.76, and a dielectric constant of approximately 25–30 KV/cm2. Thus it is similar to JP4, which has a viscosity of 0.9 cs (at 100° F.), specific gravity of 0.76 and a dielectric constant of 25–30 KV/cm2; and JP5, which has a viscosity of 1.4 cs (at 100° F.), a specific gravity of 0.81 and a dielectric constant of 25–30 KV/cm2. Although MIL-F-7024 provides an accurate simulation, like most other fluids with similar properties it has a low flash point. In fact, its flash point of approximately 105° F. makes it a hazardous material under the Department of Transportation definition, which includes liquids with flash points below 200° F. This is also true for JP4 and JP5, with flash points of 135° F. and 150° F. respectively.

The use of low flash point fluids is disadvantageous because it results in unwanted combustion when electrical elements inadvertently ignite fuel vapors. This has been a major source of operator injury and fatality and damage to the test stands. One method of addressing this problem is to "explosion proof" electrical components in/on the test stand by enclosing them in heavy aluminum or steel housings which contain the explosion or fire, thereby keeping it from propagating. National Electrical Manufacturers Association (NEMA) Type 7 enclosures are employed pursuant to the National Electrical Code (NEC), Article 500, Class I, Group D, which pertains to hazardous environments. Motors and the associated motor starters and start/stop buttons, potentiometers, tachometers, and even background lighting, are all NEMA Type 7.

Explosion proofing is disadvantageous because it does not guarantee against damage control. Unwanted combustion still occurs which damages electrical equipment contained in the NEMA Type 7 enclosures. Furthermore, explosion proofing increases test stand cost. NEMA Type 7 enclosures are approximately double the cost of NEMA Type 1 components, which are used in normal (NEC Article 400) environments. Overall expense is increased by 30–50, which is quite significant insofar as these test stands cost hundreds of thousands of dollars.

BRIEF SUMMARY OF THE INVENTION

It is an object of the invention to provide a test stand and method for calibrating aircraft fuel components which is less expensive and safer than previous designs and methods. The present invention uses a fuel look-alike to simulate the operation of an aircraft fuel system. This fuel look-alike has a viscosity, specific gravity and dielectric constant similar to that of aircraft fuel, but without its low flash point. The higher flash point permits the use of general purpose, as opposed to explosion proof, electrical components.

The fuel look-alike flows from a reservoir to a fuel pump and then to a fuel control, both of which are on test. Fuel then returns to the reservoir either through a simulated engine or a bypass system. The rotating shafts of the components on test are driven by motors, and air is used to simulate turbine pressure in the fuel control. It is operated by a single technician who controls the appropriate valves, electrical controls and temperature controls, records input pressures, flows and temperatures, and adjusts the component under test to achieve the desired output flows and pressures.

DETAILED DESCRIPTION OF THE PREFERRED EMBODIMENTS

Figure 1:
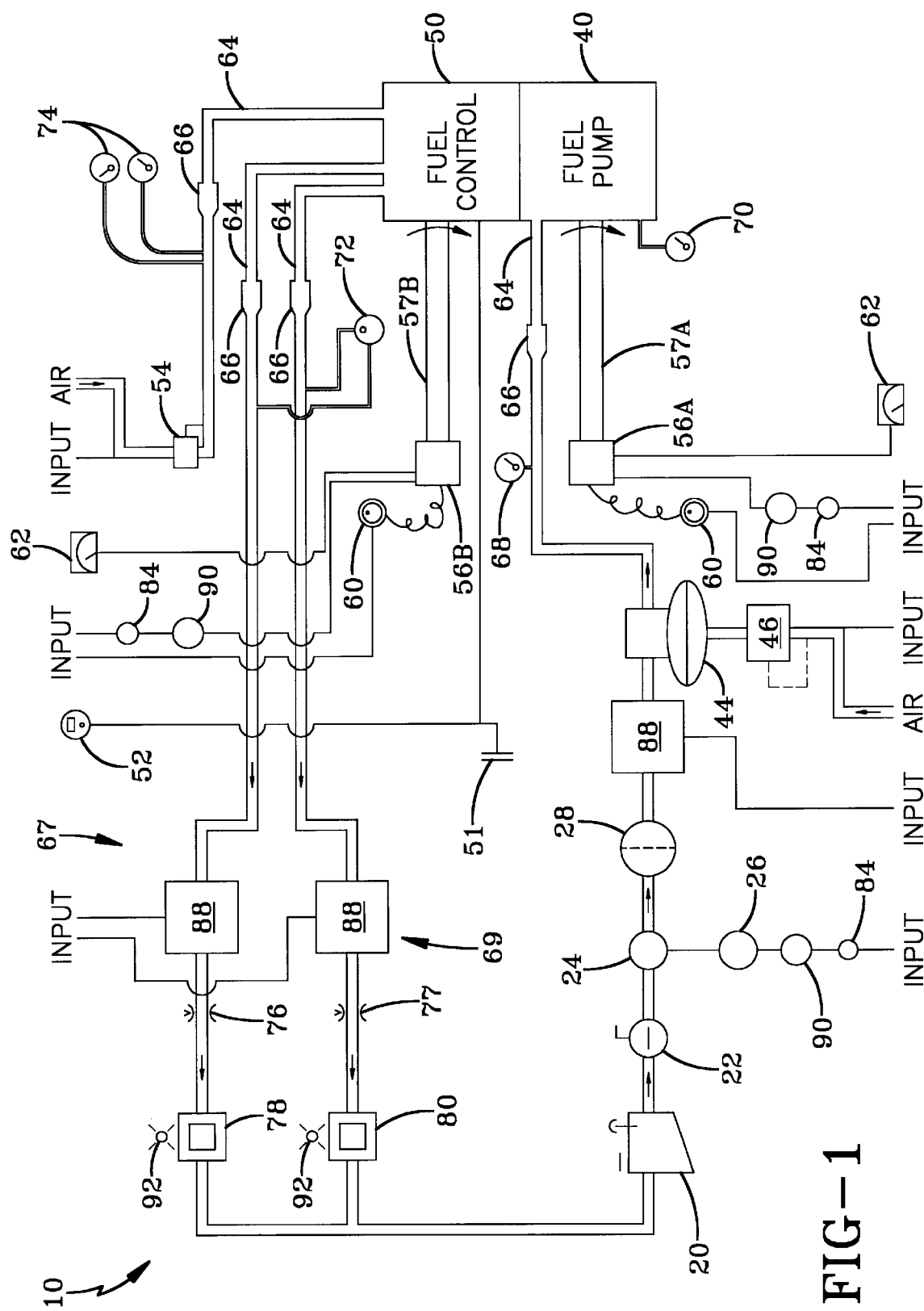
FIG. 1 is a schematic drawing of the test stand.

FIG. 1 illustrates the operation of the test stand 10, which is used to evaluate the performance of a fuel pump 40 and fuel control 50 which are being tested (on test). The test stand 10 includes a reservoir 20 which contains the aircraft fuel look-alike (hereinafter referred to simply as the fuel). The reservoir 20 is vented and preferably made of non-corrosive material such as stainless steel. Fuel is supplied from the reservoir 20 through a ball valve 22, which enables the operator to shut off the fuel supply for servicing of the test stand. The fuel then passes through a boost pump 24, which increases fluid pressure, and then on to filter 28. The boost pump 24 is driven by fuel pump motor 26, which includes motor starter 90 and operator controlled electrical start/stop and pilot light 84. The fuel pump motor and associated elements are all designed for general purposes, and therefore NEMA Type 1 components can be used.

Figure 2:
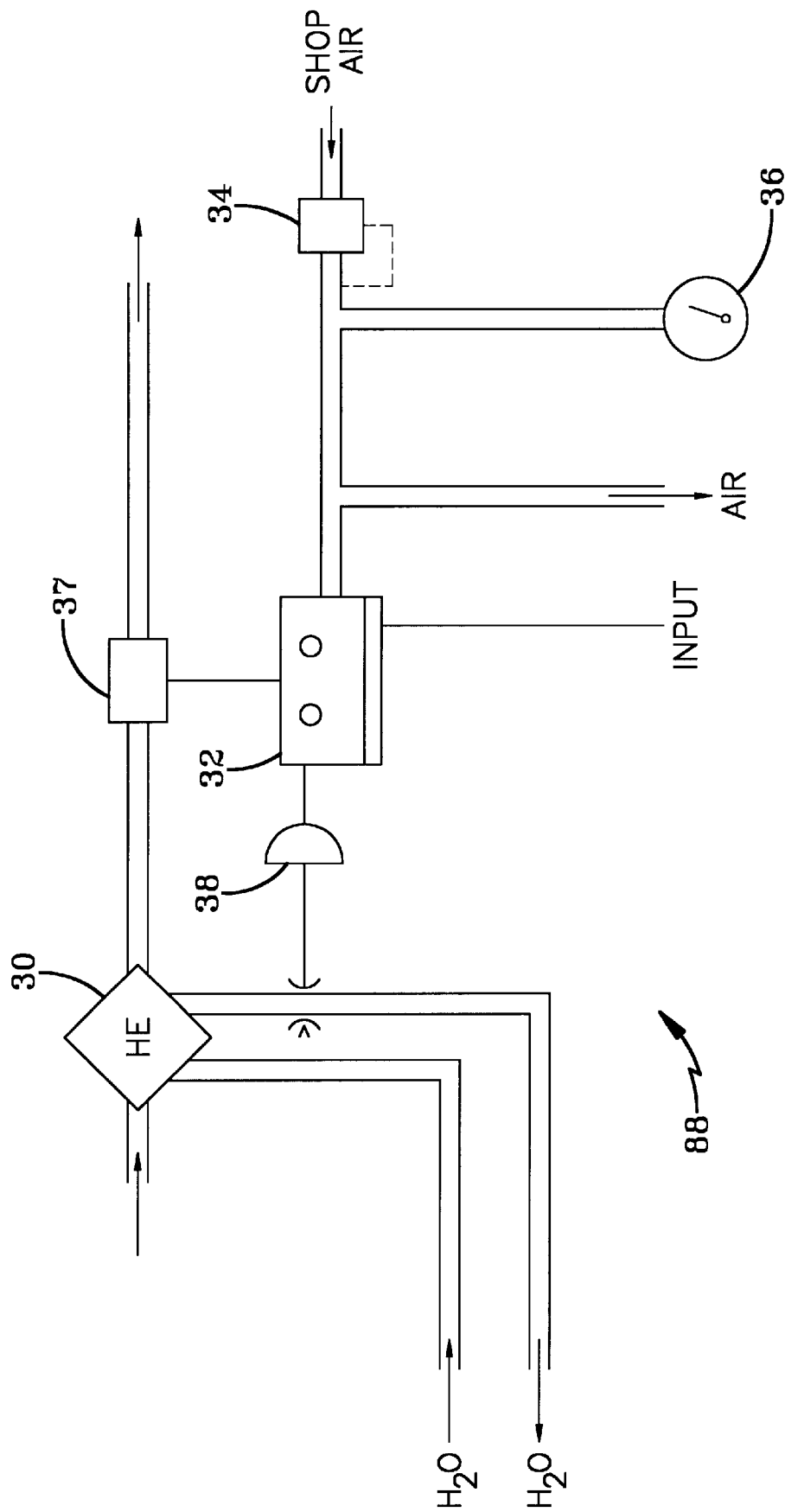
FIG. 2, is a schematic drawing of the heat exchange and temperature control system

At this point the fuel temperature is controlled by the operator with a fuel temperature control system 88, which is illustrated in detail in FIG. 2. The fuel temperature control system 88 is comprised of fuel temperature controller 32 of a type known in the art, for example Love Controls Model 26150. The operator enters the desired fuel temperature, and a temperature display (not shown) shows actual and desired fuel temperatures. Shop air enters the temperature control system through regulator 34 which controls the air pressure, and passes air pressure gauge 36. The air then passes through fuel temperature controller 32, which produces a 3–15 psi signal to water control valve 38, based upon the input from the operator and fluid temperature, which is sensed by temperature sensing element 37. The water control valve 38 then regulates cooling water flow from a heat exchanger 30. Water is supplied from and returned to the public water supply.

Returning to FIG. 1, after passing through the fuel temperature control system 88, the fuel continues to pressure controller 44, which is of a type known in the art, for example Cunico Model 5908-2". The pressure controller 44 operates according to air signals passing through valve 46, which is under operator control. The fuel then passes to the fuel pump 40 and then to the fuel control 50. Hoses 64 and port blocks 66 are used to provide the fuel pump 40 and fuel control 50 on test with the fuel supplies and returns.

The fuel control 50 requires a DC source 51 to give it a "go/no-go" signal. Volt meter 52 indicates source output. The fuel control 50 further requires air to simulate turbine engine pressure. The operator controls air pressure with air pressure regulator 54. The fuel pump 40 has a shaft 57A, which is driven by test component motor 56A. The fuel control 50 has a shaft 57B, which is driven by test component motor 56B. The test component motors 56A,56B are controlled by the operator with speed potentiometers 60. The test component motors 56A,56B each include motor starters 90 and electrical start/stop and pilot lights 84. Tachometers 62 provide the operator with the motor speeds. The test component motors 56A,56B, fuel pump motor 26, motor starters 90, tachometers 62, potentiometers 60 and start/stop and pilot lights 84 are all designed for general purposes. Fuel pressure gauge 68 indicates the fuel pump inlet pressure. Fuel pressure gauge 70 indicates the fuel pump outlet/fuel control inlet pressure. Fuel control differential pressure gauge 72 compares pressures at different points within the fuel control 50, as is understood by those skilled in the art. Air pressure gauges 74 indicate the simulated turbine pressures within the fuel control.

From the fuel control 50, fuel returns to the reservoir either through the engine system 67 or the bypass system 69. The fuel control 50 controls the proportion of fuel passing through each system with a diverter valve (not shown) within the fuel control 50. There is an engine back pressure valve 76, which controls the fuel pump outlet/fuel control inlet pressure, and a bypass back pressure valve 77 which controls the bypass pressure. Fuel loses pressure after passing through the back pressure valves 76,77, with a corresponding increase in temperature. Fuel temperature control systems 88 as illustrated in FIG. 2 offset the temperature increases so that the temperature sensitive engine flow meter 78 and bypass flow meter 80 can provide the operator with accurate readings. The flow meters are back lighted with fluorescent lights 92, of general purpose design, to enhance visibility.

Figure 3:
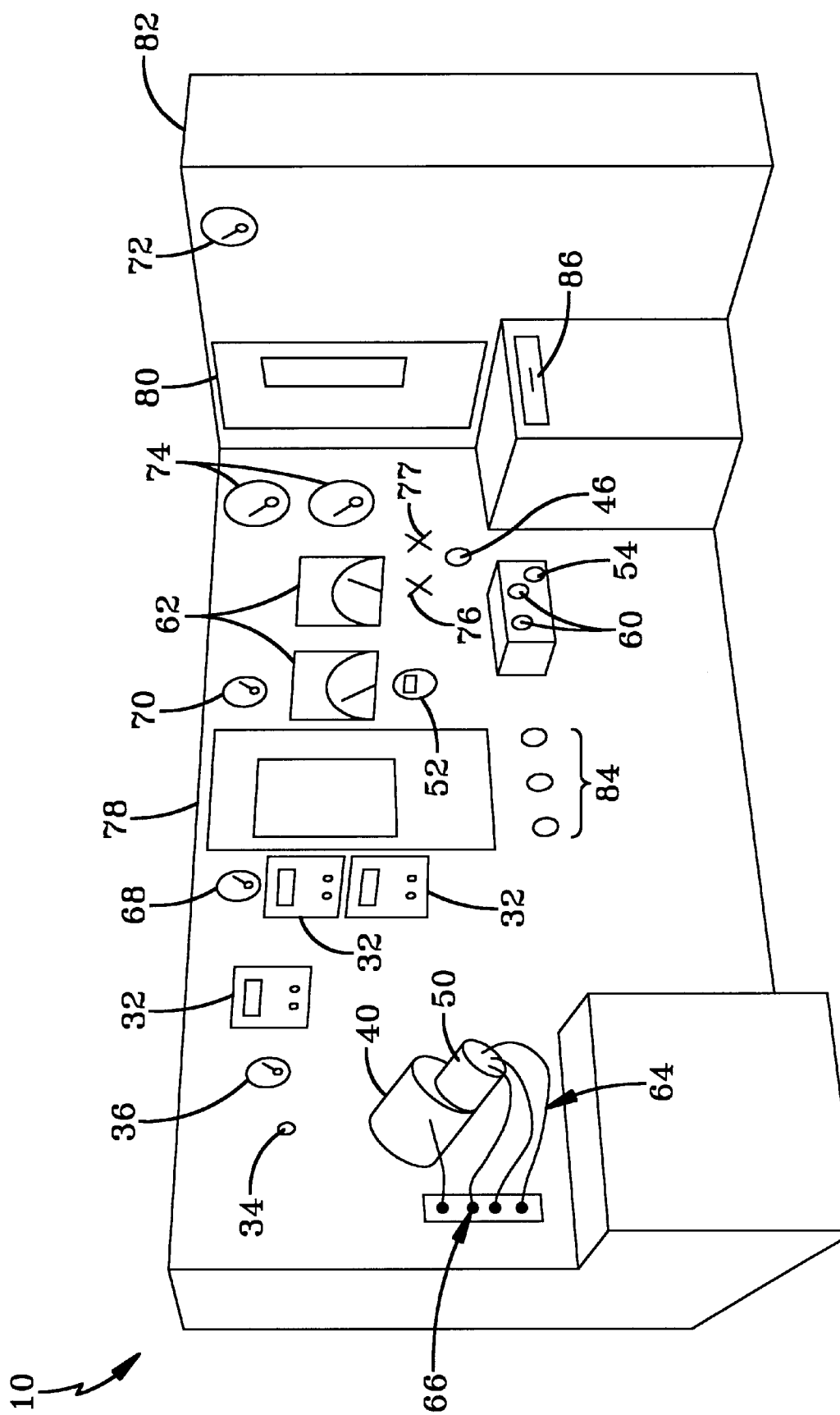
FIG. 3 is a perspective drawing of the exterior of the test stand.

FIG. 3 illustrates the exterior of the test stand. The components are contained within a housing 82 which is preferably made of sheet metal The fuel pump 40 and fuel control 50 are mounted to the front of the test stand and hoses 64 provide the fuel supplies and returns. Also visible are air pressure gauge 36, fuel pressure gauges 68, 70, fuel control differential pressure gauge 72, air pressure gauges 74, electrical stop/start and pilot lights 84, and fuel temperature controllers 32. FIG. 3 also illustrates flowmeters 78,80, potentiometers 60 and tachometers 62, air pressure regulator 54, engine back pressure valve 76, bypass back pressure valve 77, air pressure regulator 34, valve 46, and volt meter 52. A storage drawer 86 allows for storage of technical data.

The operator controls various parameters of the system to simulate an aircraft fuel system. Pressure controller 44 sets the fuel pump inlet pressure as indicated on fuel pressure gauge 68 between −10 and 100 psi. The bypass pressure and fuel pump outlet pressure are both set between 100 and 1,500 psi using the back pressure valves 76,77. The temperature of the fuel flowing through fuel pump 40 and flowmeters 78,80 is set to 80° F. (+/−2° F.) Test component motor speeds are set up to 5,000 RPM and air pressure to the fuel control is set up to 100 psi. After setting these input parameters, the operator compares the actual output parameters to the desired outputs. For the fuel pump, the output parameter is the flow through bypass flowmeter 80. For the fuel control, the output parameters are the flow through engine flowmeter 78 and the differential pressure indicated by gauge 72. The operator then adjusts the springs, shims, and relief valve orifice sizes (not shown) of the fuel pump and fuel control until the desired outputs are reached, and the calibrated elements are then ready to be used on actual aircraft.

Instead of using actual aircraft fuel such as JP4 or JP5, or a traditional fuel look-alike such as MIL-F-7024A, the present invention uses a fuel look-alike which does not have a low flash point. Instead, the fuel look-alike has a flash point above 200° F., and thus is not hazardous under DOT definition. To provide an accurate simulation, the fuel look-alike also has a viscosity below 2.8 cs (at 100° F.), a specific gravity between 0.76 and 0.81 (at 60° F./60° F.), and a dielectric constant of 25–30 KV/cm2.

A problem with finding a fluid with all of these properties is that the viscosity of a fluid generally increases with its flash point. If viscosity is too high, the fluid pressure drop across the system will be too high, resulting in an inaccurate simulation. Thus most fluids with flash points in the desired range cannot be used. However, there are exceptions to the general relationship between flash point and viscosity. An example of a liquid with all four properties in the desired range is PD-23 mineral oil, produced by Witco Chemical Corporation. PD-23 is a liquid combination of saturated aliphatic and alicyclic hydrocarbons with a specific gravity (60/60) of 0.8, a flash point of 230° F., a viscosity of 2.6 cs (at 100° F.), and a dielectric constant of 25–30 KV/cm2. Although this product is intended for use in petroleum distillate applications such as lotions, creams, household cleaners, polishes, and liquid candles, it would nevertheless be a useful fuel look-alike in the above described test stand.

Insofar as the risk of combustion is greatly reduced, the present invention uses general purpose electrical components and wiring practices, (consistent with NEC Article 400) as opposed to those classified for "hazardous locations" (NEC Article 500, Class I, Group D). Unlike previous designs, the motors, motor starters and other electrical components need not be explosion proofed, resulting in savings in the order of ⅓ to ½ over the cost of the entire test stand. Furthermore, by reducing the risk of combustion, operator safety is greatly improved.

The present invention thus provides a test stand and method for calibrating aircraft fuel components which is less costly and safer than previous designs. The invention has been described with reference to a preferred embodiment. obviously, modifications and alterations will occur to others upon the reading and understanding of this specification. It is intended to include all such alterations and modifications insofar as they come within the scope of the appended claims or the equivalents thereof.

What is claimed is:
1. A test stand for calibrating aircraft fuel components comprising:
    a test component on test,
    an incompressible fuel look-alike which passes through the test component, wherein said fuel look-alike has a flash point above 180° F., and a viscosity below 2.8 centistokes at 100° F. wherein the fuel look-alike approximates both specific gravity and dielectric constant properties of aircraft fuel, wherein said dielectric constant is between 25–30 KV/cm2, a boost pump which provides fuel look-alike pressure when the fuel look-alike passes through the test component, a first pressure controller which controls inlet pressure of the fuel look-alike into the test component, a second pressure controller which controls outlet pressure of the fuel look-alike from the test component, and a flow meter measuring flow rate of the fuel look-alike passing through the test component.

2. A test stand as in claim 1, further comprising:

a different test component on test in fluid communication with the test component, a fuel control pressure differential gauge which measures differential pressure of the fuel look-alike between predetermined points within the different test component, and a flow meter measuring flow rate of the fuel look-alike after passing through the different test component.

3. A test stand as in claim 2 wherein the test component is adjustable to obtain a predetermined flow rate.

4. A test stand as in claim 2 wherein the different test component is adjustable to obtain a predetermined flow rate and a predetermined differential pressure within the different component.

5. A test stand as in claim 3 wherein the test component further comprises a rotating shaft, wherein said shaft is driven by a general purpose electric motor.

6. A test stand as in claim 5 wherein the test component is a fuel pump.

7. A test stand as in claim 4 wherein the different test component further comprises a rotating shaft, wherein said shaft is driven by a general purpose electric motor.

8. A test stand as in claim 7 wherein the different test component is a fuel control.

9. A test stand as in claim 6 wherein the fuel look-alike has a flash point of approximately 230° F. and a viscosity of approximately 2.6 centistokes at 100° F.

10. A method for calibrating aircraft fuel components using an incompressible fuel look-alike with a flash point above 180° F., a viscosity below 2.8 centistokes at 100° F., and a dielectric constant between 25–30 KV/cm2 through a test component on test, the method comprising the steps of:

setting inlet pressure of the fuel look-alike into the test component to a predetermined value, setting outlet pressure of the fuel look-alike from the test component to a predetermined value, and measuring flow rate of the fuel look-alike after passing through the test component.

11. The method of claim 10 further comprising the steps of:

providing a different test component on test in fluid communication with the test component, measuring differential pressure between predetermined points within the different test component, and measuring flow rate of the fuel look-alike after passing through the different test component.

12. The method of claim 11 further comprising the step of adjusting the test component until a predetermined flow rate is obtained.

13. The method of claim 11 further comprising the step of adjusting the different test component until a predetermined flow rate is obtained.

14. The method of claim 13 further comprising the step of adjusting the different test component until a predetermined differential pressure within the different test component is obtained.

15. The method of claim 12 wherein the step of providing a test component further comprises the step of providing a test component with a rotating shaft, wherein said rotating shaft is driven by a general purpose electric motor.

16. The method of claim 14 wherein the step of providing a different test component further comprises the step of providing a different test component with a rotating shaft, wherein said rotating shaft is driven by a general purpose electric motor.

17. The method of claim 15 wherein the step of passing a fuel look-alike further comprises the step of passing a fuel look-alike with a flash point of approximately 230° F. and a viscosity of approximately 2.6 centistokes at 100° F.

* * * * *

UNITED STATES PATENT AND TRADEMARK OFFICE
CERTIFICATE OF CORRECTION

PATENT NO. : 6,260,426 B1  
DATED : July 17, 2001  
INVENTOR(S) : Charles Wharton and Jeffrey E. Hunt Page 1 of 1

It is certified that error appears in the above-identified patent and that said Letters Patent is hereby corrected as shown below:

Attorney Agent is: Glut, Mark O. & Lewis, John D. not Blut, Mark O.

Signed and Sealed this

Twenty-seventh Day of November, 2001

*Attest:*

*Nicholas P. Godici*

*Attesting Officer*

NICHOLAS P. GODICI  
*Acting Director of the United States Patent and Trademark Office*

UNITED STATES PATENT AND TRADEMARK OFFICE
CERTIFICATE OF CORRECTION

PATENT NO. : 6,260,426 B1  
DATED : July 17, 2001  
INVENTOR(S) : Charles Wharton and Jeffrey E. Hunt Page 1 of 1

It is certified that error appears in the above-identified patent and that said Letters Patent is hereby corrected as shown below:

<u>Title page,</u>  
Attorney Agent is: Glut, Mark O. & Lewis, John D. not Blut, Mark O.

Signed and Sealed this

Eighteenth Day of December, 2001

Attest:

*Attesting Officer*

JAMES E. ROGAN  
*Director of the United States Patent and Trademark Office*